United States Patent [19]

Dolak et al.

[11] 4,276,412
[45] Jun. 30, 1981

[54] 3-TREHALOSAMINE COMPOUNDS

[75] Inventors: Lester A. Dolak, Plainwell; Alice L. Laborde, Kalamazoo; Thomas M. Castle, Portage, all of Mich.

[73] Assignee: The Upjohn Company, Kalamazoo, Mich.

[21] Appl. No.: 76,489

[22] Filed: Sep. 17, 1979

[51] Int. Cl.³ .................. A61K 31/71; C07H 5/06
[52] U.S. Cl. ......................... 536/17 R; 424/181;
435/72; 435/100; 435/84; 435/253; 536/18;
536/115; 536/116; 536/120
[58] Field of Search .......................... 536/17 R, 18

[56] References Cited

PUBLICATIONS

Arcamone et al., "Gazz. Chim. Ital.," vol. 87, 1957, pp. 896–902.
Wolfrom, "Advances in Carbo. Chem.," vol. 18, 1963, pp. 219–221.
Uramoto et al., "Jour. Antibiotics," vol. 20, 1967, pp. 236–237.
Hanessian et al., "Jour. Antibiotics," vol. 25, 1972, pp. 683–684.
Hough et al., "J.C.S. Perkin I," 1973, pp. 287–290.
Naganawa et al., "J. Antibiotics," vol. 27, pp. 145–146, 1974.
Wright et al., "J. Chem. Soc. Chem. Commun.," 1977, pp. 710–712.

*Primary Examiner*—Johnnie R. Brown
*Attorney, Agent, or Firm*—Roman Saliwanchik

[57] ABSTRACT

Novel antibiotic 3-trehalosamine (U-59,834) producible in a fermentation under controlled conditions using the new microorganism *Nocardiopsis trehalosei* sp. nov., NRRL 12026.

This antibiotic is active against Gram-positive bacteria, for example, *Staphylococcus aureus, Bacillus subtilis,* and *Diplococcus pneumoniae.* Thus, 3-trehalosamine can be used in various environments to eradicate or control such bacteria.

Antibiotic 3-trehalosamine can be shown by the following structural formula:

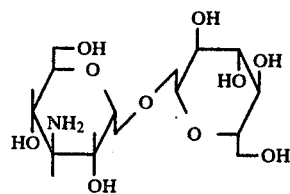

14 Claims, 4 Drawing Figures

(O-TMS, N-Trifluoroacetyl derivative)
U-59,834

3-TREHALOSAMINE COMPOUNDS

BACKGROUND OF THE INVENTION

The antibiotic of the subject invention is a new aminoglycoside antibiotic. In particular, it is considered to be 3-trehalosamine. Literature references directed to trehalosamines are as follows:

2-Trehalosamine: F. Arcamone and F. Bizioli, Gazz. Chim. Ital., 87, 896–902 (1957).

4-Trehalosamine: H. Naganawa, et al., J. Antibiotics, 27, 145–146 (1974).

6-Trehalosamine: S. Hanessian and P. Lavallee, J. Antibiotics, 25, 683–684 (1972). (Synthetically-produced).

The Altro Isomer: L. Hough, et al., J. C. S. Perkin I, 287–290 (1973). (Synthetically-produced).

Mannosylglucosaminide: M. Uramoto, et al., J. Antibiotics, 20, 236–237 (1967).

4-0-β-D-mannopyranosyl-D-mycosaminide: J. J. Wright, et al., J. Chem. Soc. Chem. Commun., 1977, 710–712 (Isolated from Antibiotic 67-121-C).

There is no known procedure for making 3-trehalosamine from any of the above or other prior art compounds.

BRIEF SUMMARY OF THE INVENTION

3-Trehalosamine is producible in a fermentation under controlled conditions using a biologically pure culture of the new microorganism, *Nocardiopsis trehalosei* sp. nov., NRRL 12026.

3-Trehalosamine is active against various Gram-positive and Gram-negative bacteria. Since it is active against *Staphylococcus aureus*, it can be used to disinfect washed and stacked food utensils contaminated with this bacterium; it can also be used as a disinfectant on various dental and medical equipment contaminated with *Staphyloccus aureus*. Further, 3-trehalosamine and its salts can be used as a bacteriostatic rinse for laundered clothes, and for impregnating papers and fabrics; and, they are also useful for suppressing the growth of sensitive organisms in plate assays and other microbiological media. Since 3-trehalosamine is active against *B. subtilis*, it can be used in petroleum product storage to control this microorganisms which is a known slime and corrosion producer in petroleum products storage.

DETAILED DESCRIPTION OF THE INVENTION

Chemical and Physical Properties of 3-Trehalosamine

Molecular Weight: 341.

Molecular Formula: $C_{10}H_{23}NO_{10}$ (mass spectra).

Infrared Absorption Spectrum

Figure 1:
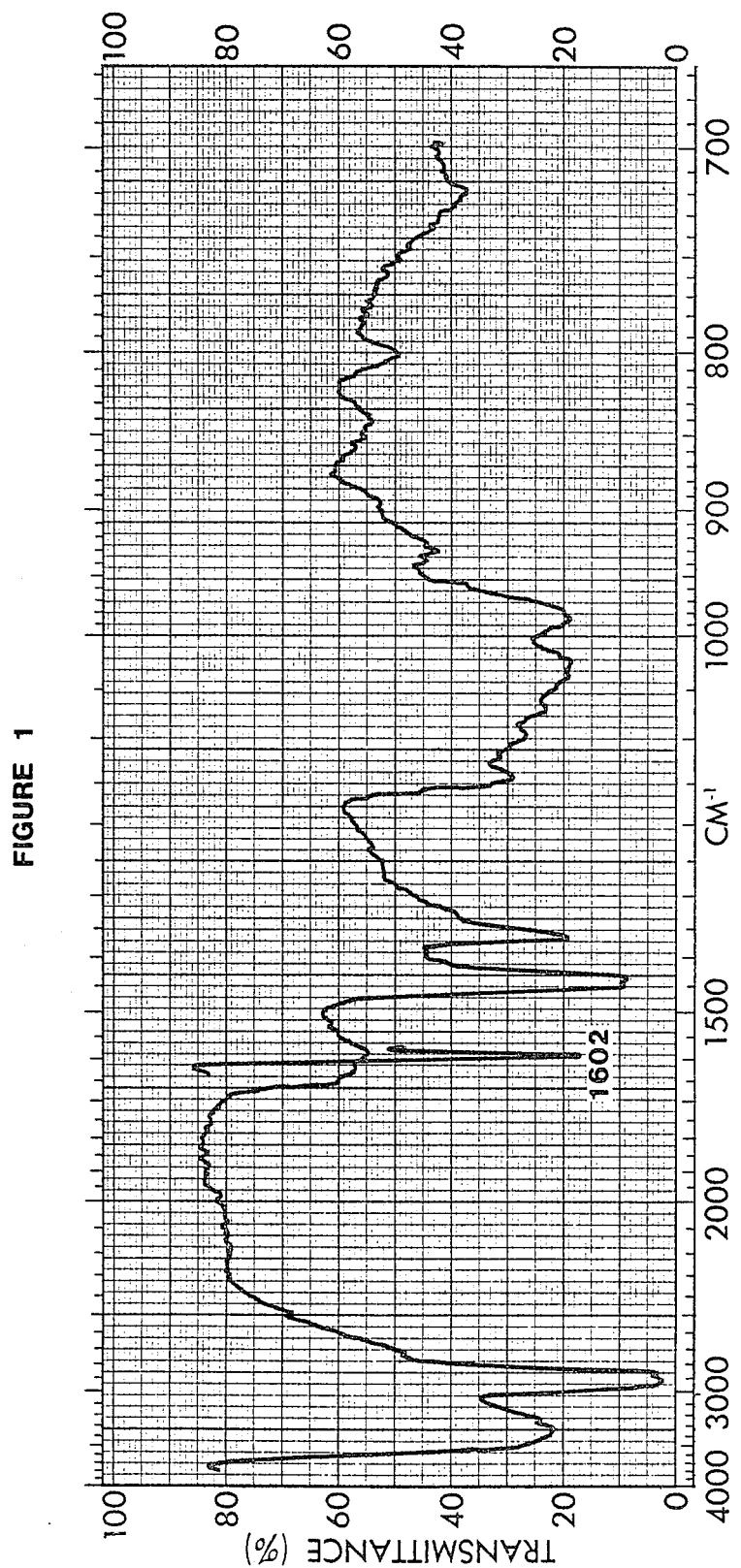

3-Trehalosamine has a characteristic infrared absorption spectrum in a mineral oil mull as shown in FIG. 1 of the drawings. Peaks are observed at the following wave lengths expressed in reciprocal centimeters.

| Band Frequency (Wave Numbers)[1] | Intensity[2] |
|---|---|
| 3196 | 18, br. |
| 2955 | 0, br |
| 2858 | 0, br. |
| 2729 | 30 |
| 2685 | 33 |
| 1659 | 39 |
| 1592 | 36 |

-continued

| Band Frequency (Wave Numbers)[1] | Intensity[2] |
|---|---|
| 1525 | 36 |
| 1461 | 3 |
| 1377 | 9 |
| 1367 | 20 |
| 1354 | 28, sh. |
| 1273 | 46 |
| 1236 | 46 |
| 1205 | 50 |
| 1151 | 20 |
| 1109 | 18 |
| 1077 | 16 |
| 1044 | 15 |
| 1031 | 16 |
| 984 | 14 |
| 933 | 36 |
| 894 | 43 |
| 843 | 47 |
| 801 | 44 |
| 763 | 44, sh. |
| 720 | 28 |
| 707 | 34, sh. |

[1]Wave numbers (cm$^{-1}$)
[2]Percent transmittance (%T), sh. = shoulder, br. = broad
Intensity at 3800 cm$^{-1}$ is 87%T.
Minimum intensity at 3723 cm$^{-1}$ is 88%T.

Solubilities: 3-Trehalosamine is soluble in water, dilute acid and dilute base.

Optical Rotation: $[\alpha]D^{25°} = +161°$ (c=13.7 mg/ml, water)

$^{13}$C-Nuclear Magnetic Resonance (NMR) Spectrum

Figure 2:
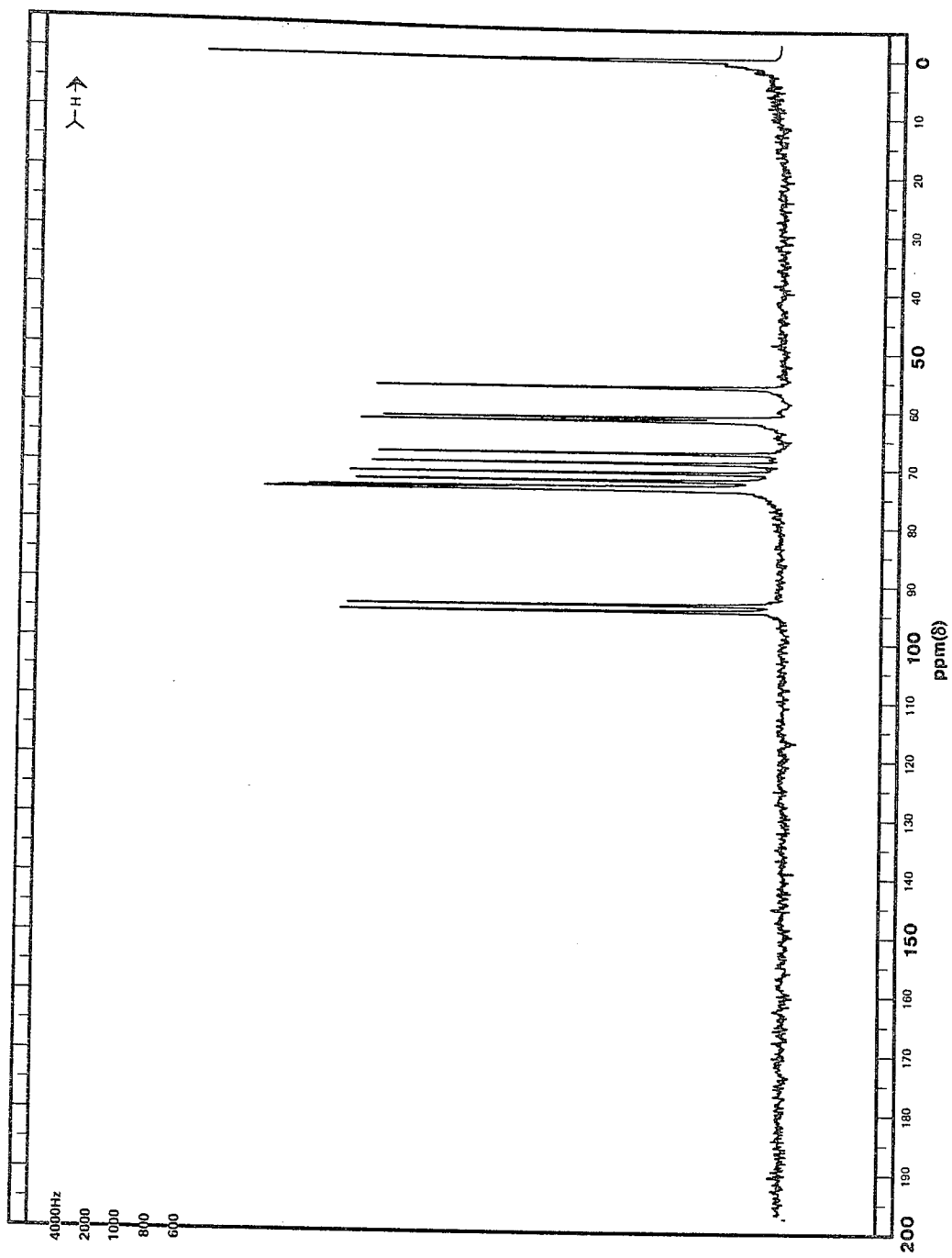

In $^{13}$C-NMR spectrum of 3-trehalosamine at 20 MHZ is shown in FIG. 2 of the drawings. The $^{13}$C-NMR spectrum was observed on a Varian CFT-20 Spectrometer on a solution (ca. 0.5 ml, ca. 200 mg/ml) of the sample of the antibiotic in deuterium oxide ($D_2O$). The spectrum was calibrated against external tetramethylsilane as 0 ppm. Frequencies were recorded in ppm downfield from tetramethylsilane.

Proton Magnetic Resonance ($^1$H—NMR) Spectrum

Figure 3:
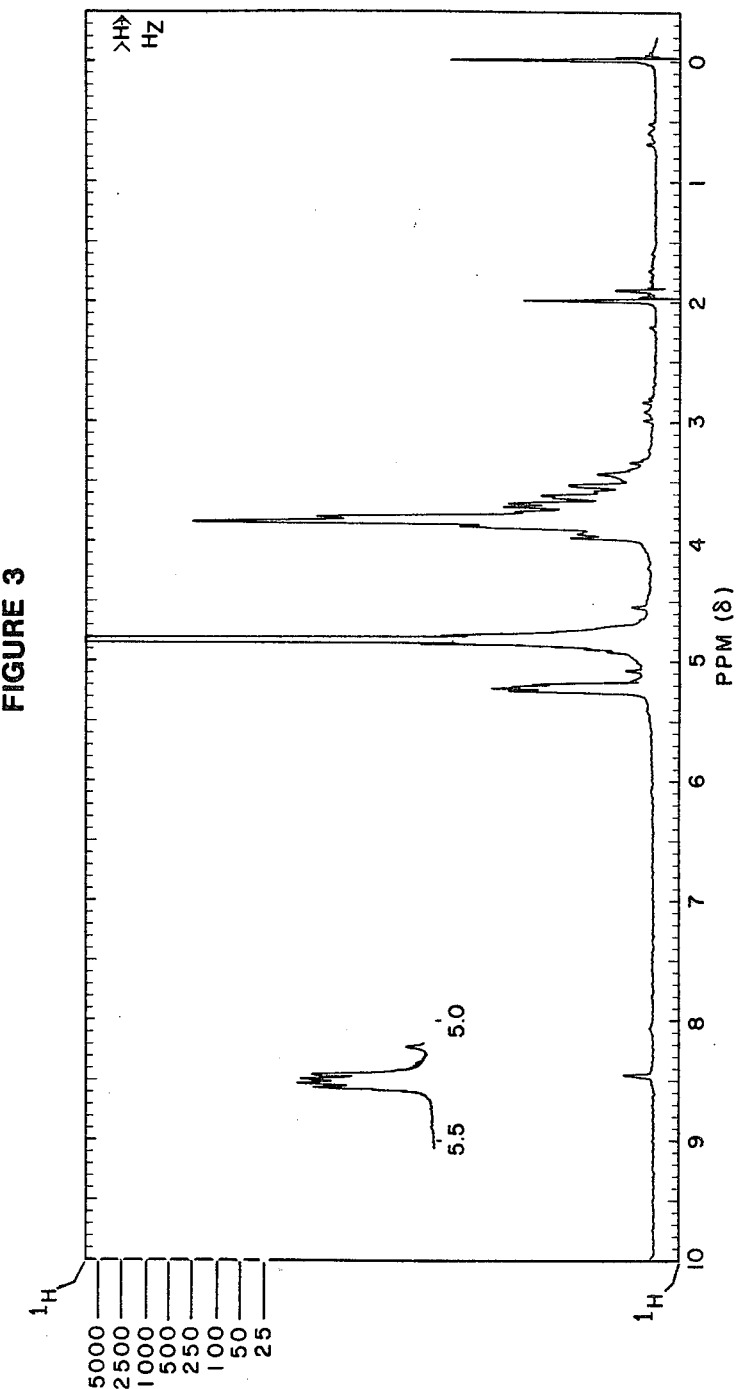

The $^1$H—NMR spectrum of 3-trehalosamine at 100 MHZ is shown in FIG. 3 of the drawings. The $^1$H—NMR spectrum was observed on a Varian XL-100-15 Spectrometer on a solution (ca. 0.5 ml, ca. 150 mg/ml) of the sample of the antibiotic in deuterium oxide ($D_2O$). The spectrum was calibrated against internal sodium 2,2-dimethyl-2-silapentane-5-sulfonate (SDSS) and frequencies were recorded in ppm downfield from SDSS.

Gas Chromatography-Mass Spectrum

Figure 4:
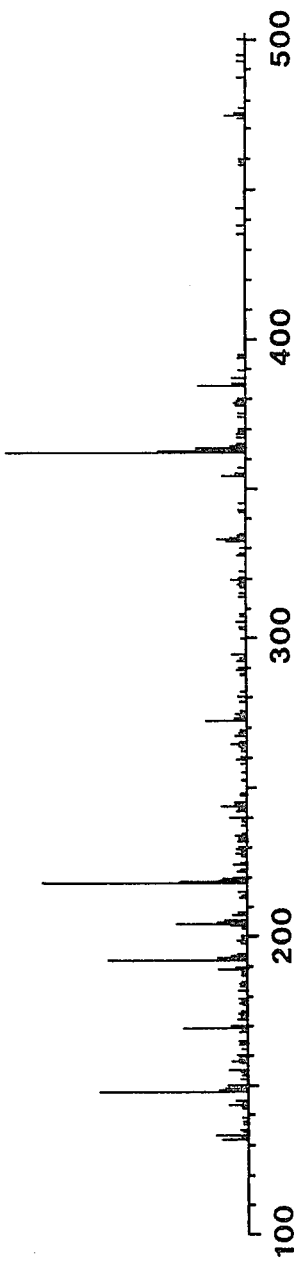

The $^{13}$C-NMR spectrum suggested the antibiotic was a disaccharide. The glycosidic bond was cleaved with methanolic hydrochloride acid using methodology well known to those skilled in the art. The constituent monosaccharides were identified as their N-trifluoroacetyl-per-O-trimethylsilyl or per-O-trimethylsilyl derivatives by comparing retention times and fragmentation patterns of similar derivatives of known sugars. The instrument used was a HP5992H GC-MS spectrometer. The analytical conditions consisted of a one meter, 3% OV-17 column with helium carrier gas and a thermal program starting at 120° and rising to 250° to 5°/min. The derivatized antibiotic had a retention time of 27.1 minutes and gave a partial fragmentation pattern (FIG. 4) consistent with a molecular weight of 941. The derivatized methyl glycosides of glucose and 3-amino- 3-deoxy-glucopyranose obtained from the methanolysis were identified in a similar manner. These monosaccharides were readily distinguishable from similar derivatives of related sugars under these conditions.

The Antibacterial Spectrum of 3-Trehalosamine

3-Trehalosamine is active against various Gram-positive and Gram-negative bacteria as shown in the following table. The testing was done on a standard microbiological disc assay system using 0.1 ml per 12.7 mm disc.

| Microorganism | Zone Size (mm) |
| --- | --- |
| Staphylococcus aureus UC 80 | 32 mm |
| Staphylococcus aureus UC 3665 | 30 |
| Klebsiella pneumoniae UC 57 | 0 |
| Bacillus subtilis UC 564 | 36.5 |
| Bacillus subtilis UC 6033 | 24 |
| Escherichia coli UC 51 | 0 |
| Sarcina lutea UC 130 | 0 |
| Proteus vulgaris UC 93 | 0 |
| Pseudomonas aeruginosa UC 95 | 0 |

| | Minimal Inhibitory Concentration ($\mu$g/ml) | |
| --- | --- | --- |
| Organism | UC | U-59,834 |
| S. aureus | 76 | >1000 |
| S. faecalis | 694 | >1000 |
| S. pyogenes | 152 | 1000 |
| D. pneumoniae | 41 | 62.5 |
| E. coli | 45 | >1000 |
| P. vulgaris | 93 | >1000 |
| K. pneumoniae | 58 | >1000 |
| S. schottmuelleri | 126 | >1000 |
| Ps. aeruginosa | 95 | >1000 |
| P. mirabilis | 6671 | >1000 |
| S. marcescens | 131 | >1000 |
| S. flexneri | 143 | >1000 |
| S. typhi | 215 | >1000 |

"UC" is a registered trademark of the Upjohn Company

Culture Collection. These cultures can be obtained from The Upjohn Company in Kalamazoo, Mich., upon request.

THE MICROORGANISM

The microorganism used for the production of 3-trehalosamine is *Nocardiopsis trehalosei* sp. nov.

A subculture of this microorganism can be obtained from the permanent collection of the Northern Regional Research Laboratory, U.S. Department of Agriculture, Peoria, Ill., U.S.A. Its accession number in this depository is NRRL 12026. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Research Laboratories.

An actinomycete isolated in The Upjohn soils screening laboratory has been characterized and found to have the macroscopic, microscopic, and whole cell hydrolysate properties of the genus Nocardiopsis [Meyer, J. 1976. Nocardiopsis, a new genus of the order Actinomycetales. Int. J. Syst. Bacteriol. 26:487–493]. The new soil isolate is compared with this strain. The new soil isolate differs from *N. dassonvillei* in its color properties (Tables 1 and 2), its failure to grow on sucrose and D-fructose in the synthetic medium of Shirling and Gottlieb (Table 3) and in its cultural characteristics (Table 4). It is further distinguished by the production of 3-trehalosamine.

This new culture is considered a member of the distinctive actinomycete genus Nocardiopsis based on its nocardioform substract mycelium, aerial mycelium with distinctive spore chain development; at first zigzag or twisted ribbon-like, subsequently constricting to form spores of irregular size (mostly elongated) with a smooth surface. Mature spore chains are not readily detected before 21 days. meso-Diaminopimelic acid is present in whole-cell hydrolysates and in cell-wall preparations. No diagnostic carbohydrates are present.

On the basis of the distinctions noted, the new culture is considered to be a new species of the genus Nocardiopsis. It is proposed that the culture be designated *Nocardiopsis trehalosei* Dietz and Li sp. nov. It is understood that this culture is the type species and that it will be considered the type subspecies should cultures with similar properties be isolated.

The taxonomic methods used herein were those cited in Dietz [Dietz, A. 1954. Ektachrome transparencies as aids in actinomycete classification. Ann. N. Y. Acad. Sci. 60:152-154; Dietz, A. 1967. *Streptomyces steffisburgenis* sp. n. J. Bacteriol. 94:2022–2026], Dietz and Mathews [Dietz, A., and J. Mathews. 1971. Classification of Streptomyces spore surfaces into five groups. Appl. Microbiol. 21:527–533], Becker et al [Becker, B., M. P. Lechevalier, and H. A. Lechevalier, 1966. Chemical composition of cell wall preparations from strains of various form genera of aerobic actinomycetes. Appl. Microbiol. 13:236–243], Lechevalier and Lechevalier [Lechevalier, H. A., and M. P. Lechevalier. 1970. A critical evaluation of the genera of aerobic actinomycetes, p. 393–405. In H. Prauser (ed.), The Actinomycetales. Veb Gustav Fisher Verlag, Jena; Lechevalier, M. P., and H. A. Lechevalier. 1970. Chemical composition as a criterion in the classification of aerobic actinomycetes. Int. J. Syst. Bacteriol. 20:487–493], and Shirling and Gottlieb [Shirling, E. B., and D. Gottlieb. 1966. Methods for characterization of Streptomyces species. Int. J. Syst. Bacteriol. 16:313–340].

*Nocardiopsis trehalosei* sp. nov, NRRL 12026.
Color Characteristics. Aerial mycelium sparse, white (W) by comparison with the Tresner and Backus [Tresner, H. D., and E. J. Backus. 1963. System of color wheels for streptomycete taxonomy. Appl. Microbiol. 11:335–338] color wheels or white to gray by comparison with the NSB Color Chips [SP 440. Color: Universal Language and Dictionary of Names. U.S. Government Printing Office, Washington, DC 20402; SRM 2106. ISCC-NBS Centroid Color Charts. Office of Standard Reference Material, Room B311, Chem. Building, National Bureau of Standards, Washington, DC 20234]. Melanin negative. Appearance on Ektachrome is given in Table 1. Reference color characteristics are given in Table 2.
Microscopic Characteristics. Aerial mycelia develop as tubes which look like twisted ribbons in about 10 days; by 21 days good spore chains have developed. These may be long and contorted. The twisted spore chains frequently give the appearance of pseudosporangia. Spores are distinct and vary greatly in length. The spore chains may collapse on the substrate and fragment or the substrate mycelium may fragment. The spores have a smooth surface. The spores may have a depressed or collapsed appearance by SEM which could also be termed ridged if the TEM carbon replica technique was used. The culture exhibits nocardioform fragmentation.

Growth on Carbon Compounds. See Table 3.

Whole Cell Analysis. meso-Diaminopimelic acid was detected. No diagnostially important carbohydrates were found.

Cell wall analysis. The results were the same as for the whole cell analysis.

Cultural and Biochemical Characteristics: See Table 4.

Temperature. Growth at 18C–45C on Bennett's, Czapek's sucrose and maltose-tryptone agars. No growth at 55C. Optimum growth at 28C–45C on Bennett's and Czapek's sucrose agars.

TABLE 1

Color characteristics* of *Nocardiopsis dassonvillei* ATCC 23213 and *Nocardiopsis trehalosei* NRRL 12026 on Ektrachrome.

| Agar Medium | Determination | N. trehalosei NRRL 12026 | | N. dassonvillei ATCC 23218 | |
|---|---|---|---|---|---|
| | | Chip | Color | Chip | Color |
| Bennett's | S | 67 | brilliant orange-yellow | 71 | moderate orange-yellow |
| | R | 67 | brilliant orange-yellow | 71 | moderate orange-yellow |
| Czapek's sucrose | S | 92 | yellow white | 32 | gray yellow-pink |
| | R | 92 | yellow white | 29 | moderate yellow-pink |
| Maltose-tryptone | S | 69 | deep orange-yellow | 72 | dark orange-yellow |
| | R | 68 | strong orange-yellow | 71 | moderate orange-yellow |
| Peptone-iron | S | 67 | brilliant orange-yellow | 72 | dark orange-yellow |
| | R | 67 | brilliant orange-yellow | 72 | dark orange-yellow |
| 0.1% Tyrosine | S | 51 | deep orange | 73 | pale orange-yellow |
| | R | 51 | deep orange | 73 | pale orange-yellow |
| Casein starch | S | 73 | pale orange-yellow | 73 | pale orange-yellow |
| | R | 73 | pale orange-yellow | 73 | pale orange-yellow |

*Color was determined by comparison with NBS Color Chips [supra].
S = Surface
R = Reverse

TABLE 3

Growth of Nocardiopsis species on carbon compounds in the synthetic medium of Shirling and Gottlieb [supra].

| Synthetic Medium (ISP-9) | N. trehalosei NRRL 12026 | N. dassonvillei ATCC 23218 |
|---|---|---|
| Negative control (No carbon cpd.) | — | — |
| Positive control | ± | + |
| L-arabinose | + + | + |
| Sucrose | — | + |
| D-xylose | + | + |
| Inositol | — | — |
| D-mannitol | + | + |
| D-fructose | — | + |
| Rhamnose | + | + |
| Raffinose | — | — |

TABLE 2

Reference color characteristics* of Nocardiopsis strains.

| Agar medium | Determination | N. trehalosei NRRL 12026 | | N. dassonvillei ATCC 23218 | |
|---|---|---|---|---|---|
| | | Chip | Color | Chip | Color |
| Bennett's | S | 92 y white | yellowish white | 90 gy. Y | grayish yellow |
| | R | 70 l. OY | light orange-yellow | 71 m. OY | moderate orange-yellow |
| | P | 70 l. OY | light orange-yellow | 67 brill. OY | brilliant orange-yellow |
| Czapek's sucrose | S | 93 y Gray | yellowish gray | 73 p. OY | pale orange-yellow |
| | R | 93 y Gray | yellowish gray | 71 m. OY | moderate orange-yellow |
| | P | — | — | 8 gy. Pl | grayish pink |
| Maltose tryptone | S | 92 y white | yellowish white | 72 y white | yellowish white |
| | R | 70 l. OY | light orange-yellow | 71 m. OY | moderate orange-yellow |
| | P | 71 m. OY | moderate orange-yellow | 67 brill. OY | brilliant orange-yellow |
| Yeast extract-malt extract (ISP-2) | S | 92 y white | yellowish white | 93 y Gy | yellowish gray |
| | R | 70 l. OY | light orange-yellow | 71 m. OY | moderate orange-yellow |
| | P | 70 l. OY | light orange-yellow | 67 brill. OY | brilliant orange-yellow |
| Oatmeal (ISP-3) | S | 93 y Gy | yellowish gray | 73 p. OY | pale orange-yellow |
| | R | 93 y Gy | yellowish gray | 73 p. OY | pale orange-yellow |
| | P | — | — | 71 m. OY | moderate orange-yellow |
| Inorganic salts starch (ISP-4) | S | 93 y Gy | yellowish gray | 90 gy. Y | grayish yellow |
| | R | 73 p. OY | pale orange-yellow | 67 brill. OY | brilliant orange-yellow |
| | P | 79 l. gy y Br | light grayish yellowish brown | 70 l. OY | light orange-yellow |
| Glycerol-asparagine (ISP-5) | S | 93 y Gr | yellowish gray | 73 p. OY | pale orange-yellow |
| | R | 73 p. OY | pale orange-yellow | 71 m. OY | moderate orange-yellow |
| | P | 70 l. OY | light orange-yellow | 71 m. OY | moderate orange-yellow |

*Determined by comparison with NBS Color Chips [supra].
S = Surface
R = Reverse
P = Pigment

TABLE 3-continued

Growth of Nocardiopsis species on carbon compounds in the synthetic medium of Shirling and Gottlieb [supra].

| Synthetic Medium (ISP-9) | N. trehalosei NRRL 12026 | N. dassonvillei ATCC 23218 |
|---|---|---|
| Cellulose | — | — |

+ + = Strong utilization
+ = Positive utilization
± = Doubtful utilization
− = Negative utilization

TABLE 4

Cultural and biochemical characteristics of Nocardiopsis strains.

| Medium | Determination | N. trehalosei NRRL 12026 | N. dassonvillei ATCC 23218 |
|---|---|---|---|
| Agar | | | |
| Peptone-iron | S | Pale gray-pink aerial growth on edge of vegetative growth | Light tan vegetative growth |
| | R | Yellow | Yellow-tan |
| | P | — | Yellow-tan |
| | O | Melanin negative | Melanin negative |
| Calcium malate | S | Colorless vegetative growth | Light tan vegetative growth |
| | R | Colorless | Pinkish tan |
| | P | — | Very light tan |
| | O | Malate not solubilized | Malate solubilized |
| Glucose asparagine | S | Colorless vegetative growth | Very light tan vegetative growth |
| | R | Colorless | Light tan |
| | P | — | Very light tan |
| Skim milk | S | Trace white aerial growth on edge of vegetative growth | Tan vegetative growth |
| | R | Light orange-tan | Tan |
| | P | Light orange-tan | Tan |
| | O | Casein solubilized | Casein not solubilized |
| Tyrosine | S | Trace pink-white aerial growth on brown vegetative growth | Brown vegetative growth |
| | R | Tan center; orange edge | Brown |
| | P | Orange-tan | Orange-tan |
| | O | Tyrosine solubilized under growth | Tyrosine solubilized under growth |
| Xanthine | S | Trace pink-white aerial growth on colorless vegetative growth | Very light yellow-tan vegetative growth |
| | R | Light yellow | Light yellow-tan |
| | P | — | Pale yellow |
| | O | Xanthine solubilized | Xanthine solubilized |
| Nutrient starch | S | Trace pink-white aerial growth on pale yellow vegetative growth | Very light yellow-tan vegetative growth |
| | R | Light yellow | Light yellow-tan |
| | P | — | Pale yellow |
| | O | Starch hydrolyzed | Starch hydrolyzed |
| Yeast extract-malt extract | S | Good cream-pink aerial growth | Brown vegetative growth |
| | R | Deep yellow | Brown |
| | P | — | Orange-tan |
| Peptone-Yeast extract-iron (ISP-6) | S | Pale yellow vegetative growth with trace white aerial growth | Cream vegetative growth |
| | R | Light yellow-range | Yellow-tan |
| | P | — | — |
| | O | Melanin negative | Melanin negative |
| Tyrosine (ISP-7) | S | Colorless vegetative growth with trace cream aerial growth | Light tan vegetative growth |
| | R | Light orange-tan | Tan |
| | P | — | — |
| | O | Melanin negative | Melanin negative |
| Gelatin | | | |
| Plain | S | Trace colorless surface growth | — |
| | P | — | — |
| | O | Gelatin not liquefied | Gelatin not liquefied |
| Nutrient | S | Trace colorless surface growth | Trace pale tan vegetative ring |
| | P | — | — |
| | O | Gelatin not liquefied | Gelatin not liquefied |
| Broth | | | |
| Synthetic nitrate | S | — | — |
| | P | — | — |
| | O | Colorless slightly flocculent No reduction | Compact bottom growth No reduction |

TABLE 4-continued

| Medium | Determination | N. trehalosei NRRL 12026 | N. dassonvillei. ATCC 23218 |
|---|---|---|---|
| | | Cultural and biochemical characteristics of Nocardiopsis strains. | |
| Nutrient nitrate | S | — | — |
| | P | — | — |
| | O | Colorless slightly flocculent bottom growth | Flocculent bottom growth |
| | | No reduction | No reduction |
| Litmus milk | S | Blue surface ring with aerial growth | Blue-gray surface ring |
| | P | Deep purple | — |
| | O | Peptonization pH 7.46 | Slight coagulation pH 7.52 |

S = Surrace
P = Pigment
R = Reverse
O = Other characteristics

The compound of the invention is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound by the invention process can be effected at any temperature conducive to satisfactory growth of the microorgansim, for example, between about 18° and 50° C., and preferably between about 20° and 28° C. Ordinarily, optimum production of the compound is obtained in about 3 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers.

Isolation can be accomplished by resin adsorption over a cationic exchange resin. The resin can be eluted with a suitable salt or buffer such as ammonium sulfate in water. Purification of the antibiotic can be accomplished by chromatography of the isolated material over a suitable chromatographic column, for example, IR-45 (OH—).

In a preferred recovery process, the compound produced by the fermentation process is recovered from the culture medium by separation of the mycelia and undissolved solids by conventional means, such as by filtration or centrifugation. The filtrate is then passed over a cationic resin, Dowex 50 W×2 ($NH_4+$) (Dow Chem. Co.) is preferred. The resin bed is washed with deionized water and eluted with a water to 1 F. $(NH_4)_2SO_4$ gradient to obtain eluates containing 3-trehalosamine.

The above eluates containing the antibiotic are pooled and desalted by passage over a column of XE-348 (Rohm & Haas resin). The column is washed with deionized water and eluted with acetone:water (1:1 v/v). The acetone is removed on a rotary evaporator and the remaining aqueous is lyophilized to a residue. The eluates are further purified by passing over silica gel chromatography from which fractions are collected and lyophilized. The lyophilized material is then suspended in deionized water and passed over an anionic resin; IR-45 (OH—) is preferred. The antibiotic is eluted from the resin with deionized water and the fractions are lyophilized to provide an essentially pure preparation of 3-trehalosamine.

With regard to the initial filtration operation, a variety of filter aids can be used with or without a flocculent to filter the fermentation beer. Also, the pH of the beer at filtration is not critical since the antibiotic remains stable and soluble at any pH from about 1 to about 11.

The first step of passing the filtered beer over a cationic resin can use other cationic resins equally well. For example, IRC-50 and Dowex 50 W×8 can be used. The ionic form can be $H^+$, $Na^+$, $NH_4^+$ or pyridinium.

The counter ion in elution can be chosen so as to obviate desalting, e.g. HCl. Ammonium formate or pyridinium acetate are volatile enough to be useful. The activity could be leached directly from the beer using charcoal or XE-348. Resins like XAD-4 or XAD-7 (Rohm and Haas) can also be used, especially at alkaline pH.

Ultrafiltration can be useful as well as gel permeation chromatography. Cellulose columns can also be used in the purification.

The anionic step can be done using other resins and crosslinkings such as Dowex 1×8 (OH—).

Water can be removed via distillation, especially on a rotary evaporator if lyophilization is not desired.

The active fractions during the recovery and purification process are determined by assay against the microorganism *Bacillus subtilis*. The assay procedure is as follows:

5.0 mls culture are centrifuged (4000×g, 10'). Serial dilutions of the supernatant solution are performed in 0.1 M phosphate buffer, pH 7.7. 0.08 ml of each dilution is applied to a filter paper disc (12.7 mm diameter, Schleicher and Schnell, Inc.-Keene, N.H.) and the disc placed onto a seeded agar tray of *B. subtilis* (UC 564). The trays are incubated at 32° C. for ca 18 hours and the zone of growth inhibition recorded.

Since 3-trehalosamine is a basic compound, procedures involving adsorption on cationic ion exchange resins and elution by organic bases or ammonia can be used to purify crude preparations of 3-trehalosamine. Also, crude preparations of 3-trehalosamine can be purified by transformation to a salt form by treatment with inorganic or organic acid. The base form of the antibiotic can be recovered by neutralization of the acid anion with ammonia or other inorganic or organic bases.

Examples of inorganic and organic acids which can be used, but which examples should not be considered limiting, are hydrochloric, sulfuric, phosphoric, acetic, succinic, citric, lactic, maleic, fumaric, pamoic, cholic, palmitic, mucic, camphoric, glutaric, glycolic, phthalic, tartaric, lauric, stearic, salicyclic, 3-phenylsalicyclic, 5-phenylsalicyclic, 3-methylglutaric, orthiosulfobenzoic, cyclohexanesulfamic, cyclopentanepropionic, 1,2-cyclohexanedicarboxylic, 4-cyclohexenecarboxylic, octadecenylsuccinic, octenylsuccinic, methanesulfonic, benzenesulfonic, helianthic, Reinecke's, dimethyldithiocarbamic, sorbic, monochloroacetic, undecylenic, 4'-hydroxyazobenzene-4-sulfonic, octadecylsulfuric, picric, benzoic, cinnamic, and like acids.

Other procedures for making certain salts are as follows. The sulfate salts can be made by using ammonium sulfate elution from a cation exchange resin. Also, the acetate salts can be made by using pyridinium acetate to elute the antibiotic from cation exchange resins. Further, the chloride salts of 3-trehalosamine can be made by using ammonium chloride to elute the antibiotic from a cation exchange resin. The sulfate salts can be converted to the chloride by passing them over an anion exchange resin, for example, Dowex 1 (Cl—) and Dowex 2 (Cl—). If the resin is used in the OH— form, the free base of 3-trehalosamine is isolated.

The salts of 3-trehalosamine can be used for the same biological purposes as the parent antibiotic.

The following examples are illustrative of the process and products of the invention, but are not to be construed as limiting. All percentages are by weight and all solvent mixture proportions are by volume unless otherwise noted.

EXAMPLE 1

A. Fermentaion

1. Preparation of Seed Inoculum

A biologically pure culture of *N. trehalosei*, NRRL 12026 is used to inoculate a 500 ml Erlenmeyer seed flask containing 100 ml of sterile medium with the following composition:

| Component | Grams/Liter Tap $H_2O$ |
|---|---|
| Cerelose | 10.0 |
| Dextrin | 20.0 |
| Corn steep liquor | 2.5 |
| $NH_4NO_3$ | 3.0 |
| NaCl | 2.0 |
| $CaCO_3$ | 5.0 |

The seed medium is adjusted to pH 7.2 with 5 N NaOH. Following sterilization, the pH of the medium is 7.4–7.7.

2. Growth of Seed Inoculum

The seed inoculum is grown for three days at 28° C. on a rotary shaker at 250 rpm.

3. Fermentation Proper

An inoculum, prepared as described above, is used to inoculate 500 ml Erlenmeyer fermentation flasks containing 100 mls of fermentation medium. The latter is identical in composition to the seed medium described above (1). Prior to sterilization the pH of the medium is adjusted to 7.2 with 5 N NaOH. Post-sterilization pH is 7.4–7.7. Fermentation flasks are inoculated at the rate of 5.0 ml seed per 100 ml fermentation medium. Incubation is at 28° C. on a rotary shaker.

A typical fermentation shows the following pattern against *B. subtilis*.

| Day | pH | BU/ml |
|---|---|---|
| 1 | 7.1 | 0 |
| 2 | 7.0 | 0 |
| 3 | 7.1 | 83 |
| 4 | 6.7 | 83 |

During the course of the fermentation, a 5.0 ml aliquot of culture medium is assayed daily. Following centrifugation (4000×g 15'), serial dilutions of the supernatant solution are made in 0.1 M phosphate buffer (pH 7.7). A unit volume (0.08 ml) of each dilution is applied to a 12.7 mm paper disc and the latter placed onto an agar tray seeded with *B. subtilis*. The agar tray is then incubated ca. 18 hours at 32° C. and the zone of inhibition recorded.

B. Recovery

Nine liters of fermentation beer (83 BU/ml *B. subtilis*), prepared as described above, pH 7.1, is filtered over a bed of Dicalite 4200 (diatomaceous earth) with about 1 l of additional Dicalite slurried in the beer at harvest pH. The filtrate is adjusted to pH 6 and passed over a column of Dowex 50 W×2 measuring 50 cm×4 cm (V=600 ml) at 3 l/hr. The column is washed with 1 l deionized water and eluted with a gradient consisting of 500 ml deionized water in the mixing arm and 3.5 l 1 F $(NH_4)_2SO_4$ in the feed arm. Fractions (50 ml each) are collected during the elution step at ca 10 ml/min during the elution step only. Fractions 12–47 show Bs zones ranging from 27 to 52 mm. These are pooled for later desalting (below).

| Sample | Volume | Bs Zone |
|---|---|---|
| FB | 9 l | 39 mm (83 BU/ml) |
| Spent | 9 l | 41 mm |
| Fractions 1–11 | 50 ml each | NZ |
| 12–47 | 50 ml each | 27–52 (max 17–30) |
| 48–100 | 50 ml each | NZ |

C. Desalting

The active fractions (12–47), obtained as described above, are passed over a column of XE-348 (Rohm and Haas) measuring 50×4 cm (V=600). The column is washed with deionized water and eluted first with 1:1 (v/v) acetone:water and then with 1:1 methanol:water.

| Sample | Volume | Solvent | Bs |
|---|---|---|---|
| Spent | 1.7 l | 1 F (NH$_2$)$_4$SO$_4$ | NZ |
| Wash | 4 l | Water | 40 mm |
| 1st Eluate | 2 l | Acetone: H$_2$O | 38 |
| 2nd Eluate | 2 l | Acetone: H$_2$O | 45 |
| 3rd Eluate | 2 l | Acetone: H$_2$O | 38 |
| 4th Eluate | 2 l | Methanol: H$_2$O | 25 |

Eluates 1–4 are pooled and stripped of organic solvent on a rotary at a bath temperature of 50°. The aqueous residue is lyophilized to give a light yellow solid which is suspended in 30 ml 0.01 N HCl and filtered through Whatman #2 filter paper.

D. Silica Gel Chromatography

The filtered solution from part C above is loaded onto a 230–400 mesh silica gel G column measuring 2.5×100 cm. This is developed with the upper phase from 2:1:1 (v/v) chloroform:methanol:17% NH$_4$OH to which 150 ml of butanol had been added per liter of upper phase. The flow rate is 10 ml/min and 50 ml fractions are collected. The fractions are assayed using 100λ per 12.7 mm disc on Bs UC 564. The antibiotic activity appears in tubes 11–15 on the tail of a yellow band which eluted starting at tube #5. Tubes 11–15 are concentrated to a gummy, hygroscopic solid using an oil pump and a rotary evaporator with a bath temperature of 50°. The 3 g tacky solid is suspended in 20 ml 0.001 N HCl and filtered through a cotton plug to remove silica gel fines. The filtrate is lyophilized to give 2.84 g tacky solid of 3-trehalosamine.

E. IR45 Retardation

The 2.8 g solid of 3-trehalosamine from above is suspended in a minimum amount of deionized water. The suspension is passed over 50 ml IR-45 (OH—) in a small column. This is eluted with water with the following results after lyophilization.

| Sample | Volume | Solids | vs Bs |
|---|---|---|---|
| Spent | 10 ml | 675 mg | 40 BU/mg |
| 2nd Fraction | 10 ml | 1.6 g | 20 BU/mg |
| 3rd Fraction | 20 ml | 70 mg | 80 BU/mg |

The 3rd fraction is almost colorless and is essentially pure 3-trehalosamine.

The designation BU, used herein, means biounit. A biounit is defined as the concentration of the antibiotic which gives a 20 mm zone of inhibition. Thus, if for example a fermentation beer, or other solution containing the antibiotic, needs to be diluted 1/100 to give a 20 mm zone of inhibition, the potency of such beer or solution is 100 BU/ml.

DERIVATIVES OF 3-TREHALOSAMINE

Acylates of 3-trehalosamine can be made as follows:
A sample of 3-trehalosamine is dissolved in an excess of a silylating reagent such as TMS-imidazole or bis-TMS-trifluoroacetamide. A catalyst such as trimethylchlorosilane and/or a base such as pyridine may be used but neither is necessary. An acylating reagent such as trifluoroacetyl-imidazole or acetic anhydride is then added. Acylation is rapid and quantitative is judged by combined gas chromatography-mass spectroscopy. The main peak observed corresponds to a hepta-trimethylsilylated N-acyl derivative of 3-trehalosamine.

Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and lower alkoxyhydrocarboncarboxylic acids include hydrocarboncarboxylic acids as given above which are substituted by one or more of halogen, nitro, hydroxy, amino, cyano, or thiocyano, or lower alkoxy, advantageously lower alkoxy of not more than six carbon atoms, for example, methoxy, ethoxy, propoxy, butoxy, amyloxy, hexyloxy, and isomeric forms thereof. Examples of such substituted hydrocarboncarboxylic acids are:

mono-, di- and trichloroacetic acid;
trifluoroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methylcyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopenanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcylic acid;

galllic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate); and the like.

The above acylates of 3-trehalosamine are useful to upgrade the parent compound, i.e. by acylating the parent compound, then removing the acyl group, the parent compound is isolated in a purer form.

The per-O-trimethylsilyl-N-trifluoroacetyl derivative can be made by the following procedure. The free base of 3-trehalosamine is heated with trimethylsilylimidazole in acetonitrile at 60° C. for about 30 minutes. Trifluoroacetic anhydride is then added and the solution is heated another 10 minutes at 60° C. The resulting derivative can be used without further purification. It is useful for assay work using gas chromatography.

Peracylates of 3-trehalosamine, for example, the peracetate, can be made by dissolving 3-trehalosamine in pyridine and adding a suitable anhydride, for example, acetic anhydride. The solution is stirred at room temperature to 100° C. for about 1 to about 24 hours. The pyridine is then evaporated on a rotary evaporator and the resulting residue is subjected to chromatography on a silica gel column to yield the desired product. The choice of the solvent to be used on the silica gel column is within the skill of those in the art using methods like thin layer chromatography (tlc) $R_f$-determination. Generally, a good solvent combination will give an $R_f$ of about 0.1 to about 0.6.

The above compounds are useful for mass spectroscopy work in that they are volatile derivatives which will fragment in a predictable way. These derivatives are also useful for proton magnetic resonance spectroscopy because the derivative is easily soluble in organic solvents.

Mixed O,N-acylates can be made of 3-trehalosamine. The acyl group is as given above. 3-Trehalosamine is dissolved in methanol or aqueous methanol. When the temperature is 0° or lower, a base, for example, triethylamine, is added. An acylating reagent, for example, an acyl halide (for example, benzoyl chloride) is then added to the solution. The reaction is allowed to warm up to about 25° C. after which the solvent is stripped on a rotary evaporator. The resulting residue is dissolved in a non-hydroxylic solvent, for example, pyridine. Next, a second acyl halide (for example, acetyl chloride) is added. The solvent is then stripped on a rotary evaporator and the resulting residue is chromatographed on a silica gel column using a solvent system which can be determined by the procedure given above. The resulting product is N-benzoyl-per-O-acetyl 3-trehalosamine. This derivative is useful in mass spectroscopy to determine location of amino groups.

Ketal derivatives of 3-trehalosamine can be made by treating the parent compound with a mixture of an aldehyde or a ketone with an acid. For example, acetone, 2,2-dimethoxypropane, 3-trehalosamine, and p-toluenesulfonic acid kept at about 25° to about 100° C. for from about 1 to about 24 hours yields the acetonide. The volatiles are then stripped on a rotary evaporator and the resulting residue is chromatographed on a silica gel column as described above.

An alkyl aldehyde of from 2 to 5 carbon atoms, inclusive, or an aryl aldehyde of from 7 to 10 carbon atoms, inclusive, can be used. Ketones can be from 3 to 8 carbons, inclusive, dialkyl, diaryl or alkylaryl.

The ketal derivatives are useful for NMR analysis of the resulting fused ring system. The derivatives selectively protect certain combinations of hydroxyl groups, for example, vicinal hydroxyl groups, leaving others available for reaction. The utility of these ketal derivatives as protecting groups is enhanced by the fact that they are easy to remove at the end of the reaction.

Cyclic carbamates, including thiono cyclic carbamates, of 3-trehalosamine can be prepared by dissolving 3-trehalosamine in a solvent combination, for example, tetrahydrofuran and 1,2-dimethoxyethane. At about 0° or lower, there is added carbonyl diimidazole (1 molar equivalent). The reaction mixture is stirred for from 1 to 24 hours and the temperature allowed to rise from 0° to about room temperature. The solvent is then stripped under a rotary evaporator and the resulting residue is subjected to silica gel column chromatography, as described above. The cyclic carbamate derivatives of 3-trehalosamine are useful to protect vicinal O—N groups. The groups protected are different from the hydroxyls protected by the above described ketal derivatives. Further, the cyclic carbamates are useful to solubilize 3-trehalosamine for proton magnetic resonance analysis.

Ethers of 3-trehalosamine can be made by dissolving 3-trehalosamine in a non-hydroxylic solvent combination, for example, tetrahydrofuran-dimethylsulfoxide. The solution is then refluxed in the presence of a base, for example, pyridine, with a large excess of methyliodide for about 1 to about 48 hours. The solvent is then stripped on a rotary evaporator and the resulting residue is subjected to silica gel chromatography, as described above. Ethers of from 1 to 8 carbon atoms, inclusive, alkyl and aryl, can be made; for example, the methyl and benzyl ether of 3-trehalosamine. The ether derivatives of 3-trehalosamine are the preferred derivatives for gas chromatography and mass spectroscopy analysis.

Oligosaccharides of 3-trehalosamine with 5 and 6 carbon sugars including the cyclitols, for example, streptamine and 2-deoxystreptamine, can be made by dissolving 3-trehalosamine or a partially protected derivative in a non-hydroxylic solvent, for example, tetrahydrofuran. To this solution is then added the sugar, for example, 2,6-diamino-2,6-dideoxy glucopyranosyl chloride in the presence of a base, for example, mercuric chloride or sodium carbonate, at 0° to about 100° C. for about 1 to about 24 hours. The solvent is then stripped on a rotary evaporator and the resulting residue is chromatographed on a silica gel column, as described above, to give 6-O-2',6' diamino-2',6' dideoxy glucopyranosyl 3-trehalosamine. These compounds are antibacterially active, and, thus, can be used for the same antibacterial purposes as the parent 3-trehalosamine compound.

All of the above disclosed derivatives of 3-trehalosamine are useful to upgrade the parent 3-trehalosamine compound. That is, by converting a preparation of 3-trehalosamine to the derivative, isolating the derivative, and then reverting back to the parent compound, a pure preparation of the parent compound is thus obtained.

Antibiotic 3-trehalosamine can be shown by the following structural formula:

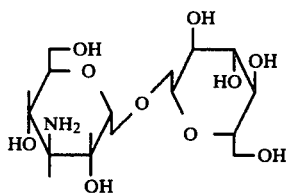

We claim:
1. Antibiotic 3-trehalosamine which can be shown by the following structural formula:

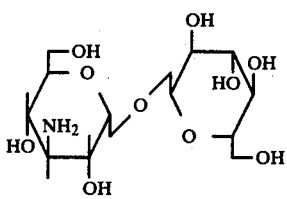

2. Acid addition salts of 3-trehalosamine, the compound of claim 1.

3. Acylates of 3-trehalosamine, the compound of claim 1, wherein said acyl group is a hydrocarbon carboxylic acid acyl of from 2 to 18 carbon atoms, inclusive; halo-, nitro-, hydroxy-, amino-, cyano-, thiocyano-, and lower alkoxy-substituted hydrocarbon carboxylic acid acyl of from 2 to 18 carbon atoms, inclusive.

4. The per acylates of 3-trehalosamine, according to claim 3.

5. The per-O-trimethylsilyl-N-trifluoroacetyl derivative of 3-trehalosamine, according to claim 4.

6. Per-acetyl-3-trehalosamine, a compound according to claim 4.

7. Mixed O,N-acylates of 3-trehalosamine, the compound of claim 1, wherein said acyl group is a hydrocarbon carboxylic acid acyl of from 2 to 18 carbon atoms, inclusive; halo-, nitro-, hydroxy-, amino-, cyano-, thiocyano-, and lower alkoxy-substituted hydrocarbon carboxylic acid acyl of from 2 to 18 carbon atoms, inclusive.

8. N-benzoyl-per-O-acetyl 3-trehalosamine, a compound according to claim 7.

9. Ketal derivatives of 3-trehalosamine, the compound of claim 1.

10. Cyclic carbamate derivatives of 3-trehalosamine, the compound of claim 1.

11. Ether derivatives of 3-trehalosamine, the compound of claim 1, wherein said ether group is from 1 to 8 carbon atoms, inclusive.

12. Permethyl ether of 3-trehalosamine, a compound according to claim 11.

13. Oligosaccharides of 3-trehalosamine, the compound of claim 1, wherein the sugar moiety is a 5 or 6 carbon sugar.

14. 6-O-2',6' diamino-2',6' dideoxy glucopyranosyl 3-trehalosamine, a compound according to claim 13.

* * * * *